United States Patent [19]
Cioca et al.

[11] 3,939,831
[45] Feb. 24, 1976

[54] PROCESS FOR PREPARING MEDICINAL DRESSINGS

[75] Inventors: Gheorghe Cioca; Nicolae Tigaeru; Agrippa Ionescu; Nicolae Chiotan; Mihai Constantinescu; Gheorghe Niculescu, all of Bucharest, Romania

[73] Assignee: Intreprinderea Flacara Rosie, Bucharest, Romania

[22] Filed: Mar. 4, 1974

[21] Appl. No.: 447,559

[52] U.S. Cl................................ 128/156; 128/260
[51] Int. Cl.² ........................................ A61L 15/00
[58] Field of Search .......... 128/155, 156, 296, 328, 128/DIG. 8, 260, 172; 131/140 P

[56] References Cited
UNITED STATES PATENTS

| 2,444,124 | 6/1948 | Wedler | 131/140 P UX |
| 2,610,625 | 9/1952 | Sifferd et al. | 128/296 |
| 3,157,524 | 11/1964 | Artandi | 128/296 |
| 3,742,955 | 7/1973 | Battista et al. | 128/DIG. 8 X |

Primary Examiner—Lawrence W. Trapp
Attorney, Agent, or Firm—Karl F. Ross; Herbert Dubno

[57] ABSTRACT

Collagen-based medicinal dressings are produced by freezing a collagen aqueous polydispersion obtained from cattle hide in a concentration of 0.66 to 2% by weight at a temperature of at most −65°C and subjecting the frozen polydispersion to vacuum at a pressure of $10^{-3}$ to $10^{-5}$ torr for a period of 24 to 48 hours while maintaining a temperature thereof of at most +35°C. The resulting spongy mass has a density of 0.03 to 0.06 gram/cm³.

4 Claims, No Drawings

PROCESS FOR PREPARING MEDICINAL DRESSINGS

FIELD OF THE INVENTION

Our present invention relates to medicinal dressings of the collagen type and more particularly to a method of making a foam or cellular collagen dressing and to a dressing made by this method.

BACKGROUND OF THE INVENTION

Collagen foam dressings have been made heretofore by a number of processes and have been found to be advantageous as skin dressings or skin plasters particularly suitable for the treatment of burns (see British Pat. No. 942,226).

In one prior-art technique a 1.2% by weight aqueous solution of collagen is homogenized and introduced into a cylinder having a fritted-glass bottom through which air or another gas is introduced under pressure to foam the collagen. The collagen is then gelled by treating it with a cadmium nitrate solution, the cadmium nitrate solution being washed out of the gel product. The result is a porous collagen foam which may be used effectively as a bandage and may include a bacteriocidal or a bacteriostatic agent. Because this collagen gel is friable and sensitive to mechanical breakdown, it is frequently covered with a nonfoamed collagen foil of tougher character. The disadvantage of this system is that it requires a relatively large number of steps and a foil overlay dense enough to obstruct secretion from the wound and hence interfere with an advantageous property of the porous collagen layer.

In another system for the formation of collagen dressings, a spongy product can be produced by freezing a collagen sol for at least 12 hours at −20°C and then eliminating the water by contacting the frozen sol with an organic solvent having an affinity for water and which does not attack the collagen. The latter treatment (water removal) is carried out in three or four successive extractions which together require about 8 hours for removal of water to the point that the product has the required spongy character. The sponge layer has a density of 0.015 to 0.6 gram/cm$^3$, is of good porosity and is a highly desirable bandage or dressing material. However, the process for making it is laborious and takes a relatively long time.

It has also been proposed to freeze an acidic collagen sol at a temperature close to the freezing point of the aqueous system and to subject the system to a high vacuum so that water is removed by sublimation. This technique has the disadvantage that it yields a product having large pores and hence little or no utility for dressing material.

OBJECTS OF THE INVENTION

Is is the principal object of the present invention to provide an improved method of making collagen-based dressing.

Another object of the invention is to provide a method for the purposes described which avoids the aforementioned disadvantages.

Still another object of the invention is to provide a high-porosity, small-pore collagen-based dressing at relatively low cost and with good mechanical and surgical properties.

DESCRIPTION OF THE INVENTION

We have found, most surprisingly, that notwithstanding earlier work with frozen collagen systems and vacuum sublimation of water therefrom that a collagen-based dressing material can be made with excellent handling and other mechanical properties, small pores but high porosity and hence with a more satisfactory density than some earlier systems without interfering with its ability to drain exudatious wounds when the dressing material is prepared by freezing a collagen polydispersion, preferably obtained from cattle hide, and of a concentration of 0.66 to 2% in water to a temperature of at most −65°C (−65°C or lower) and subjecting the same to drying by vacuum sublimation until the product has a density of about 0.03 to 0.06 gram per cm$^2$, the vacuum sublimation being carried out such that the temperature during this process does not rise beyond 35°C. We have found that a homogeneous pore distribution requires that certain time limitations be placed upon the freezing and the sublimation steps and thus it is important to carry out the freezing of the collagen polydispersion at a temperature between − 65°C and −70°C (exclusively) for a period between 2.5 and 3.2 hours (exclusively).

Furthermore, the vacuum sublimation step should be carried out at a pressure of 10$^{-3}$ torr to 10$^{-5}$ torr over a period of 24 to 48 hours.

The product may, according to another feature of the invention, contain a bacteriostatic or bacteriocidal agent which preferably is of the steroid and/or antibiotic type and/or may contain one or more agents promoting healing. These agents may be added to the polydispersion before freezing in an amount ranging between 0.5 and 5 grams per 1000 ml of the polydispersion. Preferably the agents include tetracycline (in an amount of 0.5 to 2 grams per 1000 ml of the polydispersion) and/or hydrocortisone (in an amount of 0.5 to 0.75 grams per 1000 ml). Suitable other additives include boric acid in an amount of 0.1 to 5% (preferably about 2%) by weight of the polydispersion and sodium merthiolate in an amount of 0.05 to 0.5 grams (preferably 0.1 gram per 1000 ml).

SPECIFIC EXAMPLES

Example I

1000 Ml of 0.8% collagen polydispersion (derived from cattle hide) containing 2% by weight boric acid and 0.1 gram sodium merthiolate is suggested to homogenize in a Turmix-type homogenizer until all fiber agglomerations are dispersed. The homogeneous polydispersion was placed in jars of epoxy resin which insure a uniform heat exchange with surroundings and to which the collagen solution does not adhere. The layers in each jar had a thickness of 15 mm.

The jars containing the collagen polydispersion were introduced into a freezer and maintained at a temperature of −68°C for a period of 3 hours to allow equilibration of the crystal structure of the ice. Thereupon the frozen solvent was sublimated at a vacuum of 10$^{-4}$ torr, the temperature rising from an initial value of −40°C to −50°C over a period of 30 hours, the temperature being held at 35°C during this time.

A spongy collaged material was obtained with a density of 0.03 to 0.06 gram per cm$^3$. The product was white, elastic, compressible, easy to mold, and extremely finely pored. The material was removed from the jars and placed in polyethylene bags which were sealed and sterilized by gamma radiation.

Example II

Example I was followed except that the temperature at freezing was −65°C and the frozen material was permitted to stand in the freezer for 32 hours before being removed for vacuum sublimation. Vacuum sublimation was carried out at $10^{-5}$ torr for a period of 24 hours. The polydispersion initially contained about 1 gram of tetracycline per 1000 ml of the polydispersion. The results obtained were similar to those obtained in Example I except that the antibiotic appeared to promote healing of the wound.

Example III

Another healing-promoting dressing was made using the composition of Example I to which 0.6 gram of hydrocortisone was added and modifying the process of Example I as follows:

The freezing temperature was −70°C, the freezing duration was 2.5 hours, vacuum sublimation was carried out at $10^{-3}$ torr, and the duration of vacuum sublimation was 48 hours.

Example IV

The process of Example I was carried out using a polydispersion which, in addition, contained 0.5 grams of tetracycline and 0.5 grams of hydrocortisone. Again the product was similar to that of Example I except that it had noticeable healing promotion qualities when applied to burns. In all of the examples the material had good capillitary and was useful for substantially all superficial dressing purposes.

We claim:

1. A method of making a collagen-based medicinal dressing comprising the steps of:

freezing a collagen polydispersion containing a bacteriocide, bacteriostat or healing-promotion agent in water to a temperature between −65°C and −70°C for a period of 2.5 to 3.2 hours, drying the frozen polydispersion by vacuum sublimation over a period of substantially 24 to 48 hours at a pressure of $10^{-3}$ to $10^{-5}$ torr, and maintaining the temperature during the vacuum sublimation period up to +35°C.

2. The method defined in claim 1 wherein said polydispersion has a collagen concentration of 0.66 to 2%.

3. The method defined in claim 2 wherein 0.5 to 2 grams of tetracycline is added per 1000 ml of the polydispersion.

4. The method defined in claim 2 wherein 0.5 to 0.75 grams of hydrocortisone is added per 1000 ml of the polydispersion.

* * * * *